(12) United States Patent
Matsuura et al.

(10) Patent No.: US 9,702,888 B2
(45) Date of Patent: Jul. 11, 2017

(54) SAMPLE ANALYZER, TRANSPORTING APPARATUS, AND LID PLACING TRAY

(71) Applicant: Sysmex Corporation, Kobe-shi, Hyogo (JP)

(72) Inventors: Hiroyuki Matsuura, Kobe (JP); Yasunori Kawate, Kobe (JP); Toru Mizumoto, Kobe (JP)

(73) Assignee: Sysmex Corporation, Kobe-shi (JP)

( * ) Notice: Subject to any disclaimer, the term of this patent is extended or adjusted under 35 U.S.C. 154(b) by 391 days.

(21) Appl. No.: 14/226,504

(22) Filed: Mar. 26, 2014

(65) Prior Publication Data
US 2014/0294673 A1 Oct. 2, 2014

(30) Foreign Application Priority Data
Mar. 28, 2013 (JP) .................. 2013-068148

(51) Int. Cl.
| G01N 35/04 | (2006.01) |
| G01N 35/02 | (2006.01) |
| G01N 35/00 | (2006.01) |
| G01N 35/10 | (2006.01) |

(52) U.S. Cl.
CPC .......... *G01N 35/04* (2013.01); *G01N 35/026* (2013.01); *G01N 35/1004* (2013.01); *G01N 35/1081* (2013.01); *G01N 2035/00287* (2013.01); *G01N 2035/0405* (2013.01); *G01N 2035/0415* (2013.01); *G01N 2035/0465* (2013.01)

(58) Field of Classification Search
CPC .. G01N 35/04; G01N 35/026; G01N 35/1004; G01N 35/1081; G01N 2035/0405; G01N 2035/0415; G01N 2035/0465; G01N 2035/00287; B01L 3/50825; B01L 2300/04; B01L 2300/042
See application file for complete search history.

(56) References Cited

U.S. PATENT DOCUMENTS

| 5,112,574 A | 5/1992 | Horton | |
| 5,472,669 A * | 12/1995 | Miki | ........ B67B 7/182 422/506 |
| 5,540,334 A * | 7/1996 | Haas | .......... B65D 25/108 206/446 |
| 6,673,316 B1 * | 1/2004 | Okamoto | ........... B01J 19/004 422/130 |
| 2005/0158212 A1* | 7/2005 | Yavilevich | ....... G01N 35/0099 422/400 |
| 2009/0004057 A1 | 1/2009 | Sato | |

(Continued)

FOREIGN PATENT DOCUMENTS

| EP | 0 128 778 A1 | 12/1984 |
| EP | 0 557 828 A1 | 9/1993 |

(Continued)

*Primary Examiner* — Jill Warden
*Assistant Examiner* — Benjamin Whatley
(74) *Attorney, Agent, or Firm* — Brinks Gilson & Lione (57) ABSTRACT

A sample analyzer capable of preventing the loss of lids of liquid containers used in the sample analyzer is provided. The sample analyzer 1 has liquid suctioning units 11 and 17 which are provided with suction tubes for suctioning liquid, container setting units 13 through 15 for setting a plurality of liquid containers 5 through 8 holding liquid, and lid placing sections 16a through 16c and 32 through 34 for placing lids 5a through 8a of liquid containers 5 through 8.

15 Claims, 9 Drawing Sheets

(56) References Cited

U.S. PATENT DOCUMENTS

| | | |
|---|---|---|
| 2010/0045147 A1 | 2/2010 | Harnack et al. |
| 2014/0106386 A1* | 4/2014 | Umeno .............. G01N 35/0099 435/23 |

FOREIGN PATENT DOCUMENTS

| | | | |
|---|---|---|---|
| EP | 0 869 346 A2 | | 10/1998 |
| EP | 0 882 500 A1 | | 12/1998 |
| JP | 2004-219218 A | | 8/2004 |
| JP | 2004219218 A | * | 8/2004 |
| JP | 2009-077639 A | | 4/2009 |
| JP | 2011-153960 A | | 8/2011 |
| JP | 2012-007998 A | | 1/2012 |

\* cited by examiner

SAMPLE ANALYZER, TRANSPORTING APPARATUS, AND LID PLACING TRAY

RELATED APPLICATIONS

This application claims priority under 35 U.S.C. §119 to Japanese Patent Application No. 2013-068148 filed on Mar. 28, 2013, the entire content of which is hereby incorporated by reference.

FIELD OF THE INVENTION

The present invention relates to a sample analyzer, a transporting apparatus, and a lid placing tray, and specifically relates to a sample analyzer with a container setting unit for setting a plurality of liquid containers, and a transporting apparatus and lid placing tray used by the sample analyzer.

BACKGROUND OF THE INVENTION

There are known conventional sample analyzers having a container setting unit for setting a plurality of liquid containers (for example, refer to US Patent Application publication No. 2009/004057).

US Patent Application publication No. 2009/004057 discloses a sample analyzer configured to measure a specimen prepared by mixing a sample and reagent, and which is provided with a container setting unit for accommodating in a refrigerated state a plurality of reagent containers which contain reagents to be used in measurements. The reagent container setting unit is configured to receive each type of reagent container with the lid opened in an internal empty space which is closed off by a cover and case section. The reagent in the reagent container is aspirated by a reagent dispensing probe and discharged therefrom for mixing with a sample.

In the conventional sample analyzer disclosed US Patent Application publication No. 2009/004057, when the analyzer is no longer in use following the completion of measurements, the reagent containers are removed from the reagent container setting unit, the reagent containers then are capped to prevent evaporation and deterioration of the reagent, and the reagent containers are stored in a refrigerator within the facility. In this case, the user recaps the reagent containers removed for current use after measurement operations have been completed each day. However, once a lid has been removed from a reagent container, the user may have forgotten where the removed lid was placed when stowing away the container, or the user simply may lose the lid. Note that in the case of this sample analyzer, liquids such as cleaning solution and dilutant, calibrators used for accuracy control, and controls (standard specimens) also are used and may require handling similar to the reagent containers. Therefore, it is imperative to not lose the lids of the various liquid containers, including those of the reagent containers.

SUMMARY OF THE INVENTION

The scope of the present invention is defined solely by the appended claims, and is not affected to any degree by the statements within this summary.

A first aspect of the present invention is a sample analyzer, comprising:

a container setting unit for setting a plurality of liquid containers accommodating liquids;

a detecting unit configured to perform a measurement operation for a sample using the liquid;

a liquid suctioning unit including a suction tube for suctioning the liquid from at least one of the plurality of liquid containers; and a lid placing section for placing a lid of at least one of the plurality of the liquid containers.

A second aspect of the present invention is a transporting apparatus, comprising:

a transport path configured to move a sample container accommodating a sample to the measuring device which performs a measurement operation on a sample using at least one of a plurality of liquids;

a lid placing section for placing a lid of at least one of a plurality of liquid containers accommodating the plurality of liquids.

A third aspect of the present invention is a lid placing tray which is removably installed in the sample analyzer for measuring a sample using a liquid, the sample analyzer provided with a container setting unit for setting a plurality of liquid containers accommodating liquids to be used in the measurement of the sample, and a liquid suctioning unit for suctioning a liquid by inserting a suction tube in a liquid container set on the container setting unit, the lid placing tray comprising:

a placing area which accommodates lids of a plurality of containers; and a dividing member for dividing the placing area into a plurality of areas corresponding to the plurality of liquid containers.

DETAILED DESCRIPTION OF THE PREFERRED EMBODIMENTS

The preferred embodiments of the present invention will be described hereinafter with reference to the drawings.

The embodiments of the present invention are described below based on the drawings.

The general structure of the sample analyzer 1 of an embodiment of the present invention is described below with reference to FIGS. 1 through 9.

Figure 1:
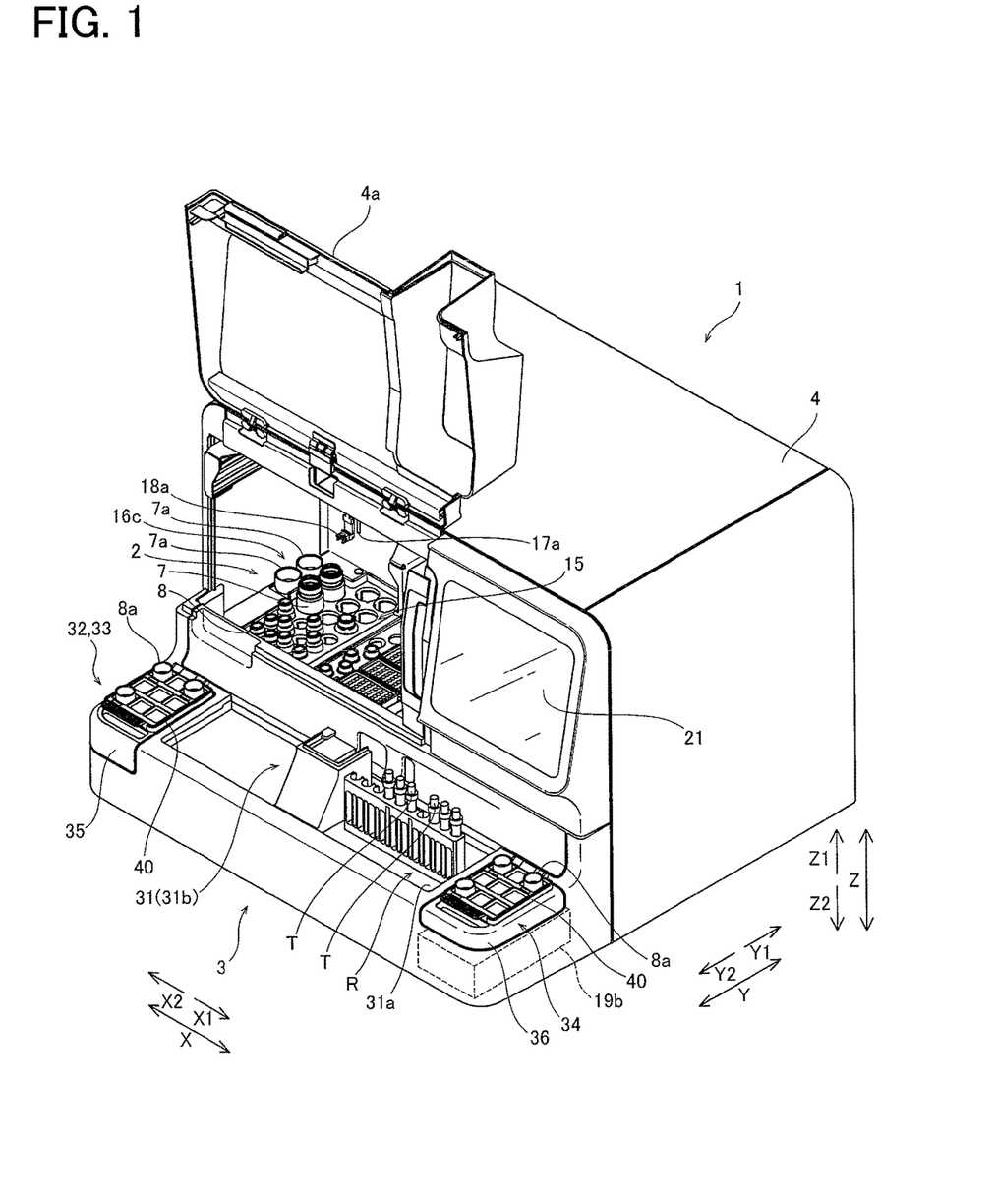
FIG. 1 is a perspective view showing the structure of the sample analyzer of an embodiment of the present invention.
Figure 2:
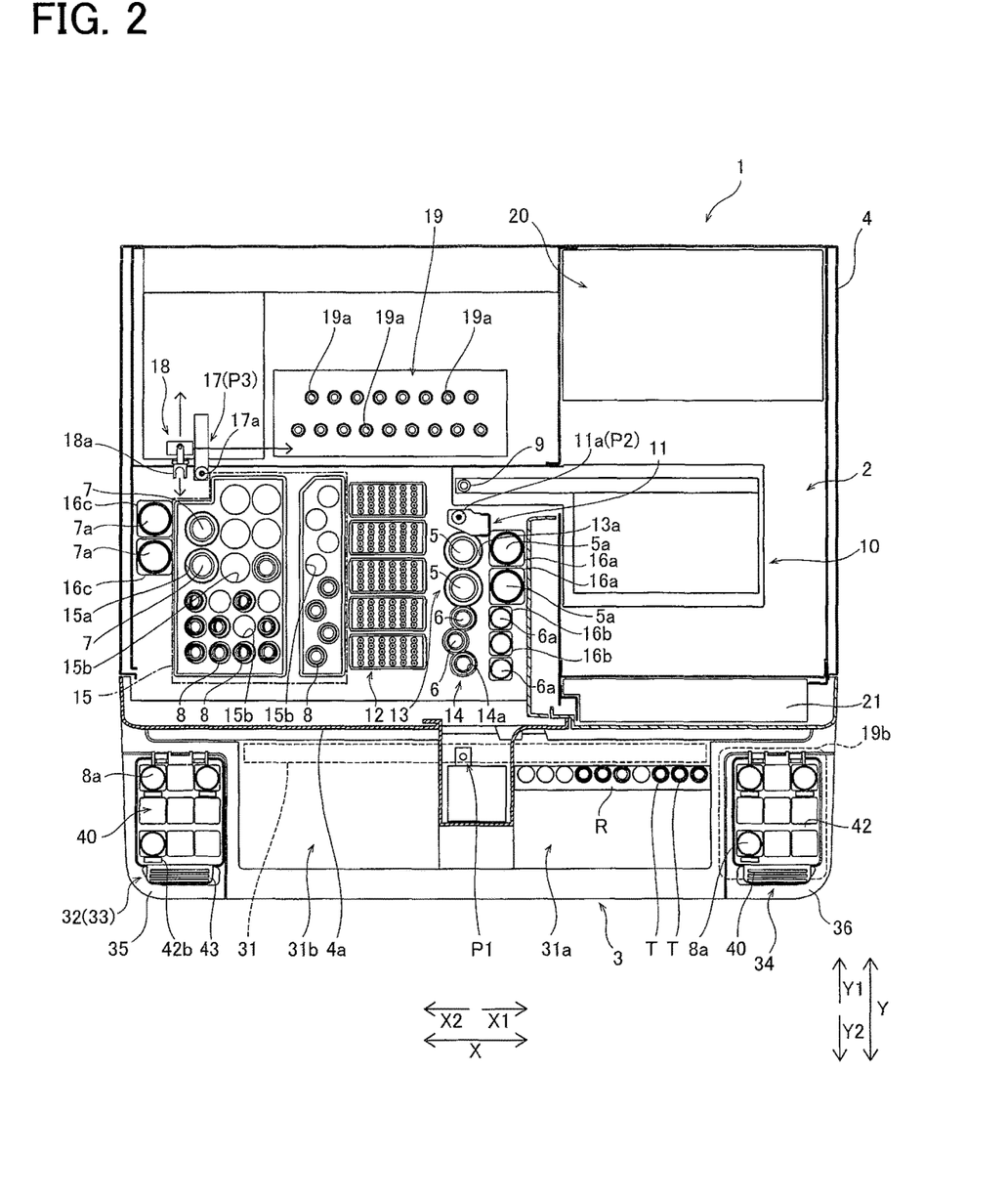
FIG. 2 is a brief schematic plan view showing the structure of the sample analyzer of an embodiment of the present invention.

The sample analyzer 1 of the embodiment of the present invention is configured by a measuring device 2, and a transporting apparatus 3 arranged on the front side of the measuring device 2 as shown in FIG. 1. The measuring device 2 is housed within a housing 4 of the apparatus body. In the present embodiment, lid placing sections, which accommodates lids 5a through 8a of a plurality of liquid containers 5 through 8 accommodating liquid such as reagent, washing solution and diluting liquid used in sample measurement operations in the measuring device 2, are provided inside and outside of the housing 4, as shown in FIGS. 1 and 2. Specifically, the sample analyzer 1 is provided with lid placing sections 16a through 16c disposed within the housing 4, and lid placing sections 32 through 34 disposed outside the housing 4.

The measuring device 2 has the functions of measuring a specimen prepared by mixing a sample and reagents, and analyzing the components of the sample. As shown in FIG. 2, the measuring device 2 includes cuvette supplier 10, sample suctioning unit 11, sample plate setting unit 12, container setting units 13 through 15, lid placing sections 16a through 16c, reagent suctioning unit 17, cuvette moving unit 18, detecting unit 19, control unit 20, and display unit 21.

The measuring device 2 is configured to obtain optical information related to a sample by performing optical measurements of a specimen prepared from a sample supplied from the transporting apparatus 3. In the sample analyzer 1 of the present embodiment, a sample received from a sample container T on the transporting apparatus 3 and dispensed into a cuvette 9 as a reaction container is subjected to optical measurements by the measuring device 2.

The cuvette supplier 10 is configured to accommodate a plurality of cuvettes 9, and supply the cuvettes 9 sequentially one at a time to a predetermined position.

The sample suctioning unit 11 is provided with a suction tube 11a as a pipette for suctioning and discharging a sample, and is configured to be movable within a predetermined region which contains a sample suctioning position P1 and a sample dispensing position P2 via a moving mechanism that is not shown in the drawing. The sample suctioning unit 11 suctions the sample from the sample container T which was transported to the sample suctioning position P1 on the transport path 31 of the transporting apparatus 3. The sample suctioning unit 11 is configured to discharge the sample into a cuvette 9 disposed at the sample discharging position P2. The sample suctioning unit 11 is also configured to suction washing solution and diluting liquid from the washing solution container 5 set on the container setting unit 13 and the diluting liquid container 6 set on the container setting unit 14. Thus, the sample suctioning unit 11 functions as a sample suctioning unit to suction a sample from the sample container T, and a liquid suctioning unit to suction liquid from the washing solution container 5 and the diluting liquid container 6.

Sample plates having a plurality of holes are aligned on the sample plate setting unit 12. The sample suctioning unit 11 is configured to collectively dispense a sample for each analysis item in the sample plate setting unit 12 when there are several analysis items for the same sample and a plurality of specimen corresponding to these analysis items must be prepared.

The container setting units 13 and 14 are arranged centrally in the width direction of the sample analyzer 1, and the container setting unit 15 is arranged in an area on the left side (X2 direction side) facing the front (door 4a side) of the sample analyzer 1. Each type of liquid containers set in the container setting units 13 through 15 is set therein with the lid removed. The liquid accommodated within these liquid containers is suctioned by inserting the suction tube 17a of the reagent suctioning unit 17 or the suction tube 11a of the sample suctioning unit 11 through the opening at the top of the containers. In the present embodiment, lid placing sections 16a, 16b, 16c are disposed near the container setting units 13, 14, 15 to accommodate the lids of the liquid containers, that is, the lids of the washing solution container 5, diluting liquid container 6, and washing solution container 7, respectively. The lid placing sections 16a, 16b, 16c are placing areas formed on the inner bottom surface of the inside of the housing 4, and are configured to be adjacent to the liquid containers of the corresponding liquid containers, that is, the washing solution container 5, diluting liquid container 6, and washing solution container 7 set in the liquid container setting units 13, 14, 15. Note that the washing solution containers 5, diluting liquid container 6, washing solution containers 7, and reagent containers 8 are generally referred to as "liquid containers."

The container setting unit 13 includes two large mounting apertures 13a for inserting the washing solution containers 5. The washing solution within the washing solution container 5 is used to wash the suction tube 11a of the sample suctioning unit 11. The mounting apertures 13a are provided aligned along the front-to-back direction (Y direction) of the sample analyzer 1. The lid placing section 16a is a square area for placing the lid 5a of the washing solution container 5, and two lid placing sections 16a are provided to correspond to the two mounting apertures 13a, so as to be adjacent to each mounting aperture 13a in the X1 direction. The lid placing section 16a is sized to match the size of the lid 5a, and has a concave shape to restrict the movement of the lid 5a in the horizontal direction.

The container setting unit 14 includes three mounting apertures 14a for inserting diluting liquid containers 6. The three mounting apertures 14a are aligned along the Y direction at the front side (Y2 direction side) of the two mounting apertures 13a. The lid placing section 16b is a square area for placing the lid 6a of the diluting liquid containers 6, and three lid placing section 16b are provided to correspond to the three mounting apertures 14a, so as to be adjacent to each mounting aperture 14a in the X1 direction. Therefore, the container setting units 13 and 14, and the lid placing sections 16a and 16b are aligned in two rows in the Y direction. Note that the lid placing section 16b is sized to match the size of the lid 6a, and has a concave shape to restrict the movement of the lid 6a in the horizontal direction.

The container setting unit 15 is configured to accommodate a plurality of the large washing solution containers 7, and a plurality of reagent containers 8 which accommodate various kinds of reagent that are mixed to the sample when preparing the specimen for analysis from the sample. Specifically, the container setting unit 15 is provided with two large mounting apertures 15a for two washing solution containers 7, and mounting apertures 15b, which are different from the two large mounting apertures 15a, for intermediate or small reagent containers 8. The washing solution within the washing solution container 7 is used to wash the suction tube 17a of the reagent suctioning unit 17. There are a total of 26 mounting apertures 15b for setting various types of reagent containers 8. The mounting apertures 15a are aligned in the Y direction at the X2 direction end of the container setting unit 15. The lid placing section 16c is a square area for placing lids 7a of the large washing solution containers 7, and there are two lid placing sections 16c aligned in the Y direction corresponding to the two mounting apertures 15a so as to be adjacent to the each mounting aperture 15a in the X2 direction. The lid placing section 16c is sized to match the size of the lid 7a, and has a concave shape to restrict the movement of the lid 7a in the horizontal direction. The lids 8a of the intermediate or small reagent containers 8 set in the mounting apertures 15b are placed in the lid placing sections 32 through 34 provided on the outside of the housing 4, as will be described later.

The container setting units 13 through 15 have a cooling function of refrigerating and maintaining the liquids within the liquid containers 5 through 8 set in the container setting units 13 through 15 at a predetermined temperature via a refrigeration unit that is not shown in the drawing.

The reagent suctioning unit 17 has a suction tube 17a used as a pipette for dispensing reagent, and is configured to be movable within a range which includes a reagent dispensing position P3 and above (Z1 direction) the container setting unit 15 via a moving mechanism which is not shown in the drawing. The reagent suctioning unit 17 is configured to suction reagent from a targeted reagent container 8 using the suction tube 17a, and discharge the reagent to a cuvette 9 disposed at the reagent dispensing position P3. The reagent suctioning unit 17 also is configured to suction washing solution from the washing solution container 7 set in the container setting unit 15. The reagent suctioning unit 17 therefore functions as a liquid suctioning unit to suction liquid from the washing solution container 7 and the reagent container 8.

The cuvette moving unit 18 has the functions of removing a cuvette 9 from the cuvette supplier 10, and moving the cuvette 9 to each of the various units, that is, the sample dispensing position P2, reagent dispensing position P3, and detecting unit 19 and the like. The cuvette moving unit 18 has a catcher 18a which holds the cuvette 9 and is movable. The cuvette moving unit 18 moves the catcher 18a by a moving mechanism not shown in the drawing, so that the sample and reagent in the cuvette 9 is mixed, or the cuvette 9 is removed or installed.

The detecting unit 19 has the functions of heating the specimen for analysis prepared by mixing the reagent with the sample, and performing optical measurements of the sample. The detecting unit 19 has a plurality of cuvette holes 19a for inserting cuvettes 9. The specimen in the cuvette 9 held in the cuvette hole 19a is heated to a predetermined temperature by a heating mechanism not shown in the drawing to induce a reaction between the reagent and the sample. The detecting unit 19 is configured to irradiate the specimen in the cuvette 9 with measurement light guided from a light source 19b through an optical fiber or the like. The detecting unit 19 has a built-in photoreceptor element (not shown in the drawing) to receive the light irradiated on the specimen, and outputs detection signals corresponding to the amount of received light detected by the photoreceptor element.

The obtained detection signal is output to the control unit 20. The control unit 20 is configured to analyze the amount and degree of activity of specific substances in the sample based on the obtained detection signals. The control unit 20 has the functions of displaying various screens containing analysis results on the display unit 21 which is arranged on the X1 direction side of the front of the housing 4 and perform operation controls of each part of the measuring device 2 and the transporting apparatus 3.

The transporting apparatus 3 is configured to supply the sample to the measuring device 2 by transporting a rack R holding a plurality (maximum of 10 in the present embodiment) of the sample containers T containing samples to the sample suctioning position P1 of the measuring device 2. The transporting apparatus 3 includes a transport path 31 for transporting the rack R to the measuring device 2, and a plurality (3 in the present embodiment) of lid placing sections 32 through 34.

The transport path 31 extends in the horizontal direction (X direction), and connects the rack supplier 31a on the X1 direction side and the rack collector 31b on the X2 direction side. The rack R holding the sample containers T is set in the rack supplier 31a. The rack supplier 31a has the function of sequentially supplying the set racks R to the transport path 31. The transport path 31 has the function of transporting the rack R received from the rack supplier 31a to the sample suctioning position P1. The rack collector 31b has the function of collecting from the transport path 31 the rack R holding the sample containers T from which the samples have been suctioned.

Figure 3:
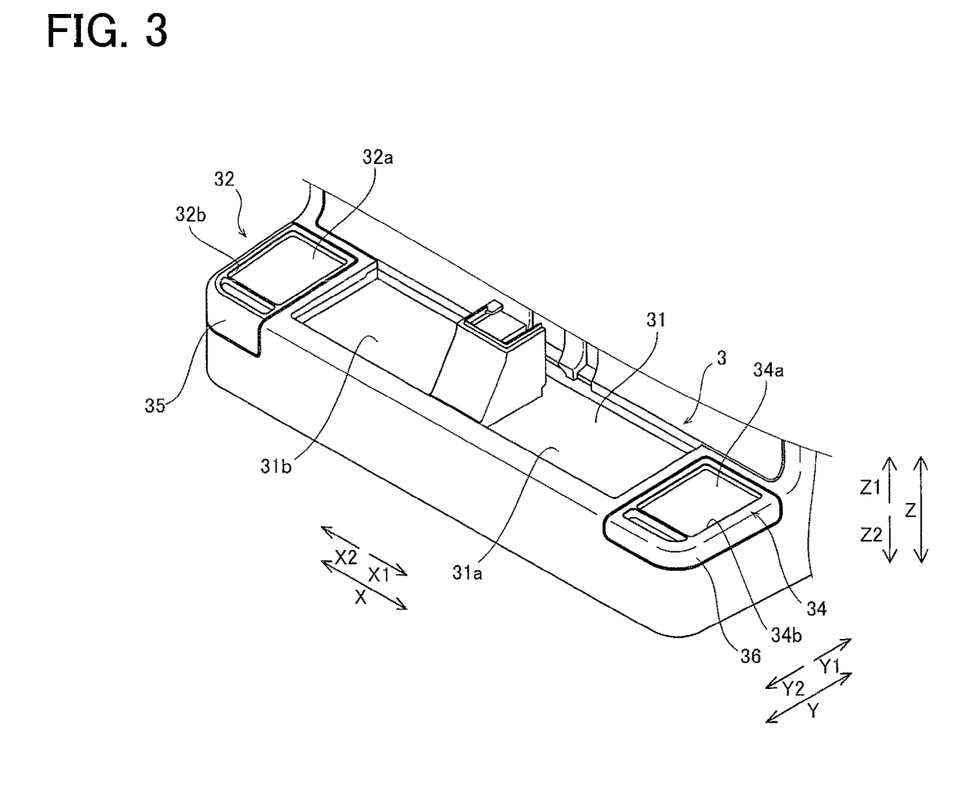
FIG. 3 is an enlarged perspective view showing the lid placing section of the transporting apparatus.
Figure 4:
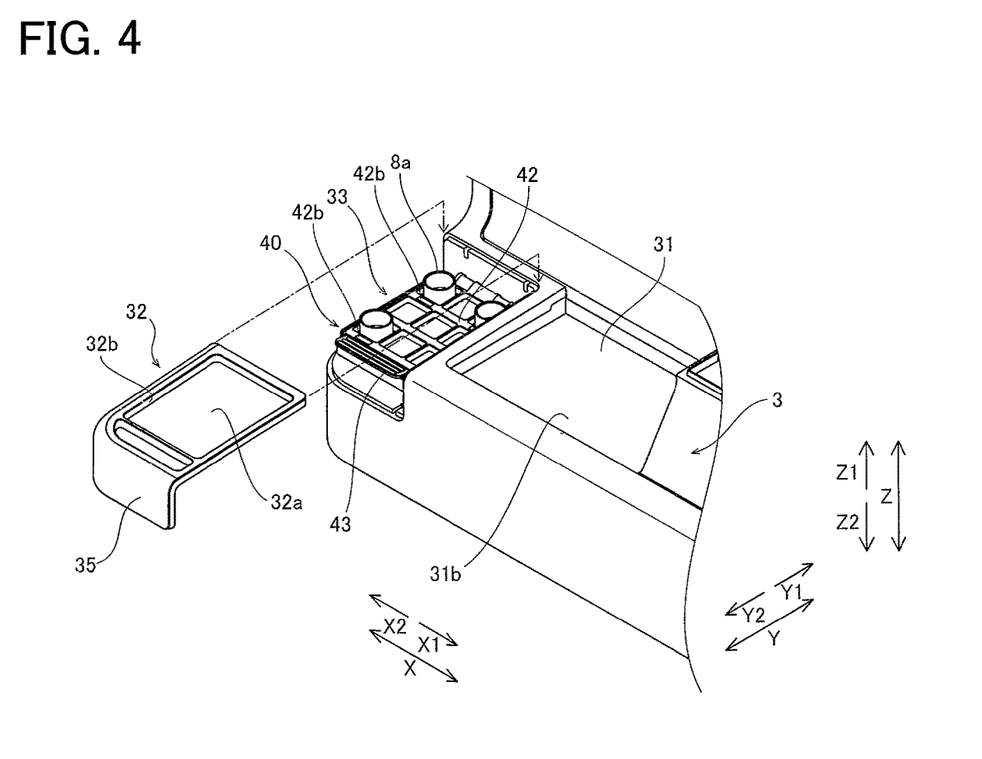
FIG. 4 is an enlarged perspective view showing the cover removed from the lid placing section of the transporting apparatus.

As shown in FIGS. 1 and 2, the lid placing sections 32 through 34 are provided in the transporting apparatus 3 on the front side (Y2 direction side) from the container setting unit 13 on the outside of the housing 4. The lid placing sections 32 through 34 also are provided in different regions than the region in the transport path 31. Specifically, the lid placing sections 32 through 34 are aligned in the X direction with the transport path 31, and are disposed at positions on the outside positions in the X direction of the transport path 31 along the transport path 31 of the transporting apparatus 3, as shown in FIGS. 3 and 4. The lid placing sections 32 through 34 are respectively positioned on bilateral sides so as to sandwich the transport path 31 therebetween at positions on the outside of the transport path 31 in the X direction, and positioned at both ends in the longitudinal direction of the transport path 31 as the X direction of the transporting apparatus 3. The lid placing section 33 (refer to FIG. 4) has a cover 35 which covers the lid placing section 33, and the lid placing section 32 is provided on the top surface of the cover 35. In the present embodiment, therefore, the two lid placing sections, which includes the lid placing section 32 disposed on the top surface of the cover 35 and the lid placing section 33 disposed inside the cover 35, are arranged on the X2 direction side, whereas the lid placing section 34 is singly arranged on the X1 direction side. Note that the lid placing section 34 on the X1 direction side is arranged on the top surface of the light source cover 36 which covers the light source 19b (refer to FIG. 2).

Note that the housing 4 of the sample analyzer 1 has a door 4a, which opens and closes the interior of the housing 4 to install and remove the liquid containers 5 through 8 in the container setting units 13 through 15, as shown in FIG. 1. The door 4a is arranged on the X2 direction side, which is the same side as the container setting unit 15 in the planar view shown in FIG. 2. Therefore, the lid placing sections 32 and 33 on the X2 direction side of the transporting apparatus 3 are arranged the front side (Y2 direction side) from the container setting unit 15 and on the same side (X2 direction side) as the door 4a and the container setting unit 15.

Figure 9:
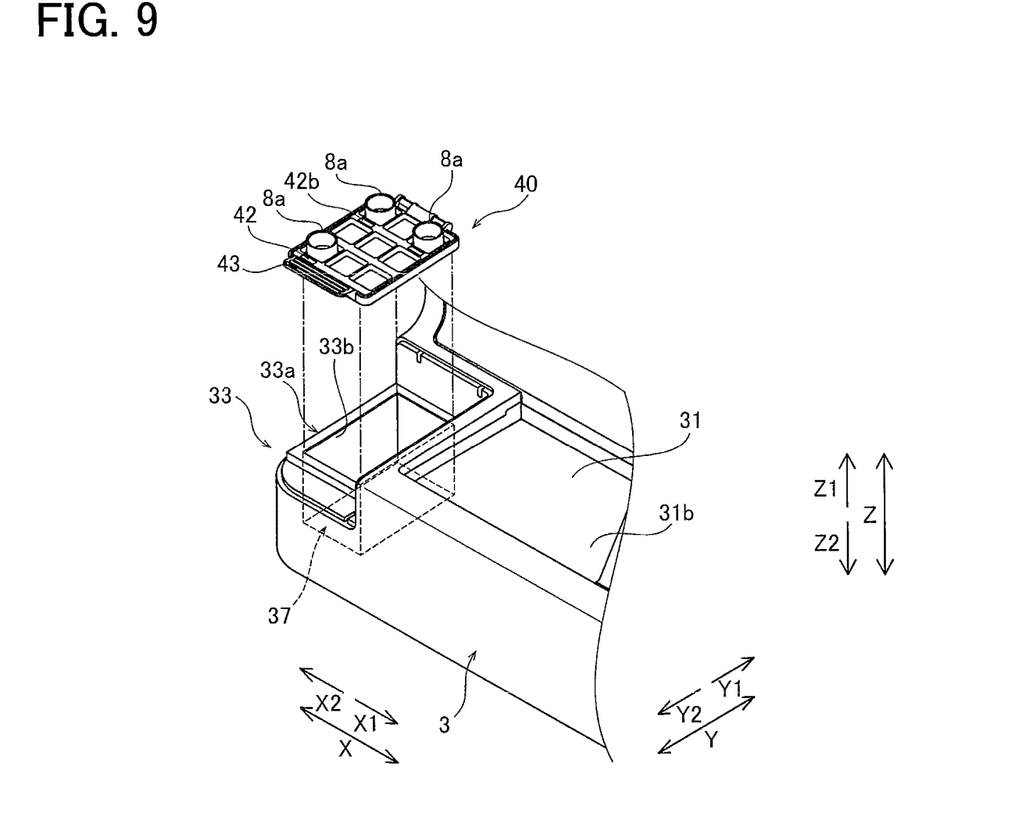
FIG. 9 is an enlarged perspective view showing the storage compartment provided in the transporting apparatus.

Each of the lid placing sections 32 through 34 provided at three locations includes a tray 40 which has an area for placing a plurality of lids 8a, and tray placing sections 32a through 34a for removably installing the tray 40 (refer to FIGS. 3 and 9). Therefore, a total of three trays 40 can be simultaneously installed in the transporting apparatus 3. The trays 40 in the respective lid placing sections 32 through 34 are identical and mutually interchangeable. The trays 40 installed in the lid placing sections 32 through 34 are provided to place the lids 8a of the reagent containers 8 which have relatively small lids (that is, small to intermediate in size) among the lids of the plurality of liquid containers.

Figure 5:
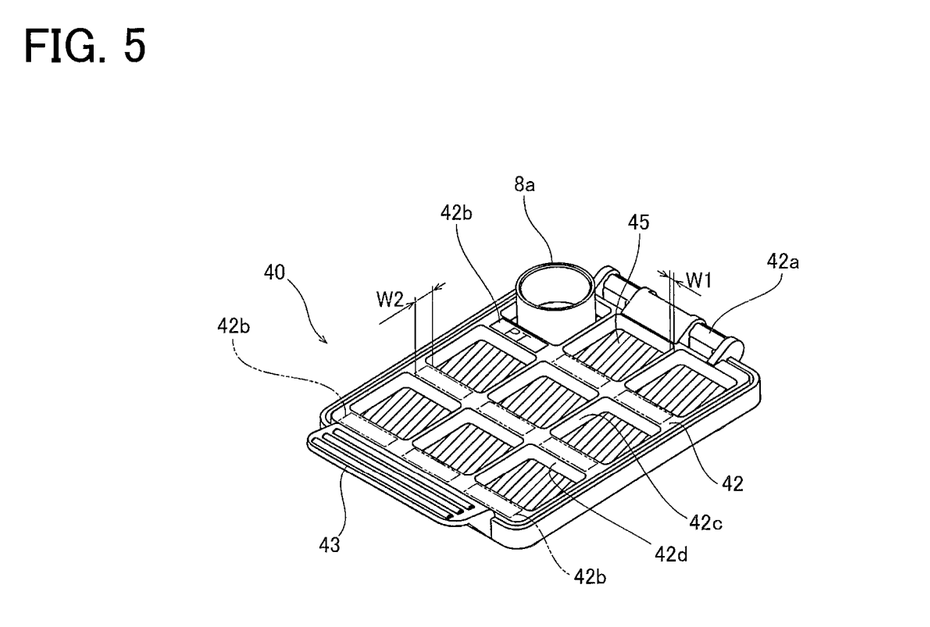
FIG. 5 is a perspective view showing the tray provided in the lid placing section of the transporting apparatus.
Figure 6:
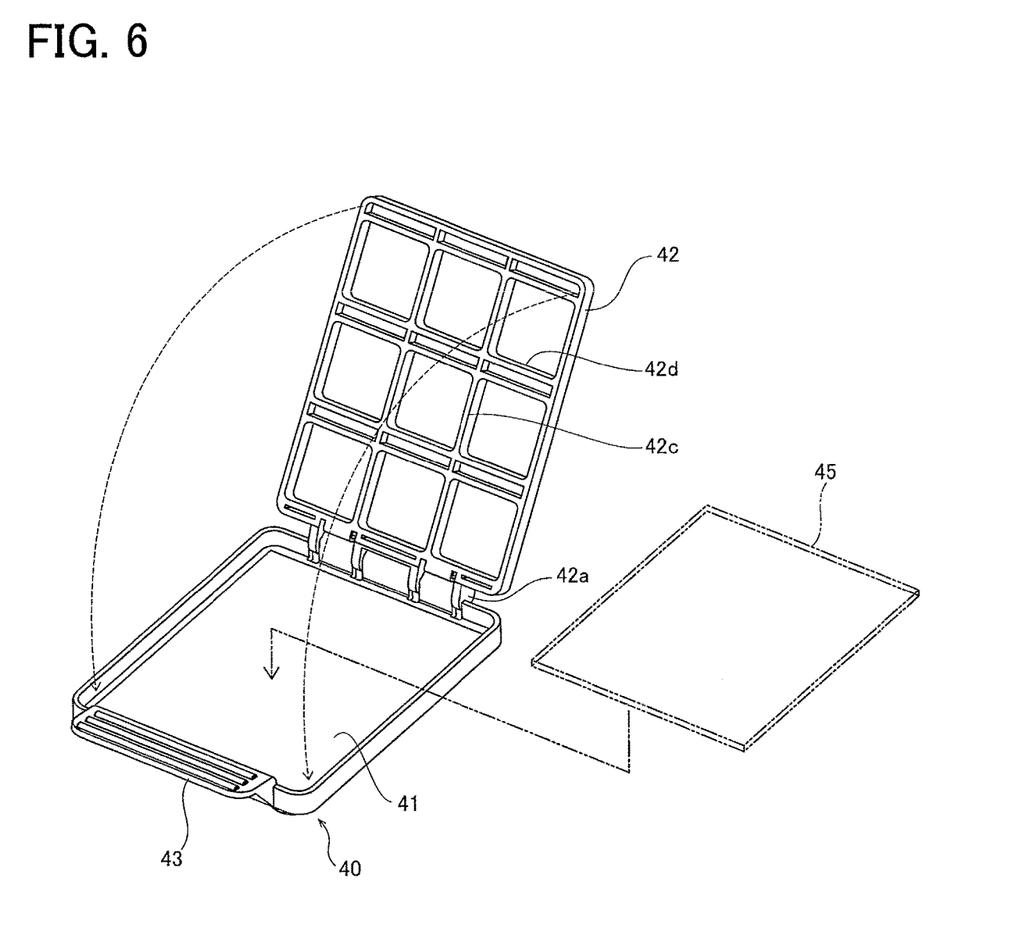
FIG. 6 is a perspective view showing the opened dividing member of the tray shown in FIG. 5.

As shown in FIGS. 5 and 6, the tray 40 is square in shape, and has a shallow bottom surface 41 (refer to FIG. 6) as the placing area of the lid 8a. The tray 40 therefore has a concave shape for placing the lid 8a on the bottom surface 41. The tray 40 is provided with a dividing member 42 used to divide the placing area on the bottom surface 41, a handle 43 for carrying the tray 40, and convex feet 44 facing downward from the under-surface of the bottom surface 41 (refer to FIG. 7).

As shown in FIG. 6, reagent can be caught and prevented from flowing out to the outside of the tray 40 even when reagent remaining on the lid 8a spills on the bottom surface 41 because the circumference of the bottom surface 41 is circumscribed by side walls. Therefore, malfunctions caused by spilling of the reagent on the transporting apparatus 3 is prevented. Note that the tray 40 can be washed when reagent adheres to the bottom surface 41.

The dividing member 42 is connected to the top of the tray 40 so as to be openable and closable relative to the tray 40. Specifically, the dividing member 42 is connected to the tray 40 through a rotating shaft 42a along the short edge of the tray 40, and is openable and closable relative to the tray 40 when rotated in upward and downward direction by pivoting on the rotating shaft 42a. The dividing member 42 is formed as a lattice so as to divide the placing area of the tray 40 into a plurality of areas. In the present embodiment, the dividing member 42 is formed in a lattice which divides the placing area into nine areas in a 3×3 pattern, such that a single tray 40 can classify and accommodate a total of none lids 8a in the divided area. Note that spilling the reagent adhered within the lid 8a is prevented because the lids 8a can be turned over in each divided area, as shown in FIG. 5.

As shown in FIG. 5, the top surface of the dividing member 42 is provided with display areas 42b corresponding to each divided area and which show the types (names) of the reagents accommodated in the reagent containers 8 on which the lids 8a are to be installed. That is, the dividing member 42 is formed so that the width W2 of the lateral lattice part 42d is larger than the width W1 of the lattice part 42c in the longitudinal direction, and the top surface area of the wide width lattice part 42d becomes the display area 42b. The user manages the association between the divided areas and the lid 8a placed in the divided area by adhering a seal member printed with the name of the reagent in the reagent container 8 and directly entering the reagent name in the display area 42b. Note that the dividing member 42 is configured to allow erasure of the entered text even when the reagent name is directly entered in pen. Therefore, the reagent name can be quickly applied by the user even, for example, when the user of the sample analyzer 1 changes to another person.

The tray 40 is configured to hold an absorbing member 45 by opening the dividing member 42, arranging an absorbing member 45 on the bottom surface 41 between the tray 40 and the dividing member 42, then closing the dividing member 42, as shown in FIG. 6. The absorbing member 45 is provided to absorb droplets of condensation and liquid reagent adhered to the lid 8a. The absorbing member 45 is not particularly limited insofar as it is an absorbent sheet, and a cleaning cloth such as waste paper, non-woven fabric, or felt may be used. Note that the hatch marks shown in FIG. 5 are provided to the absorbing member 45 for facilitating understanding.

The handle 43 is formed to extend from the end of the tray 40. The handle 43 is formed with a wide profile extending substantially over the length of the short edge on one side of the square tray 40. The handle 43 functions as a user grip area when carrying the tray 40.

Figure 7:
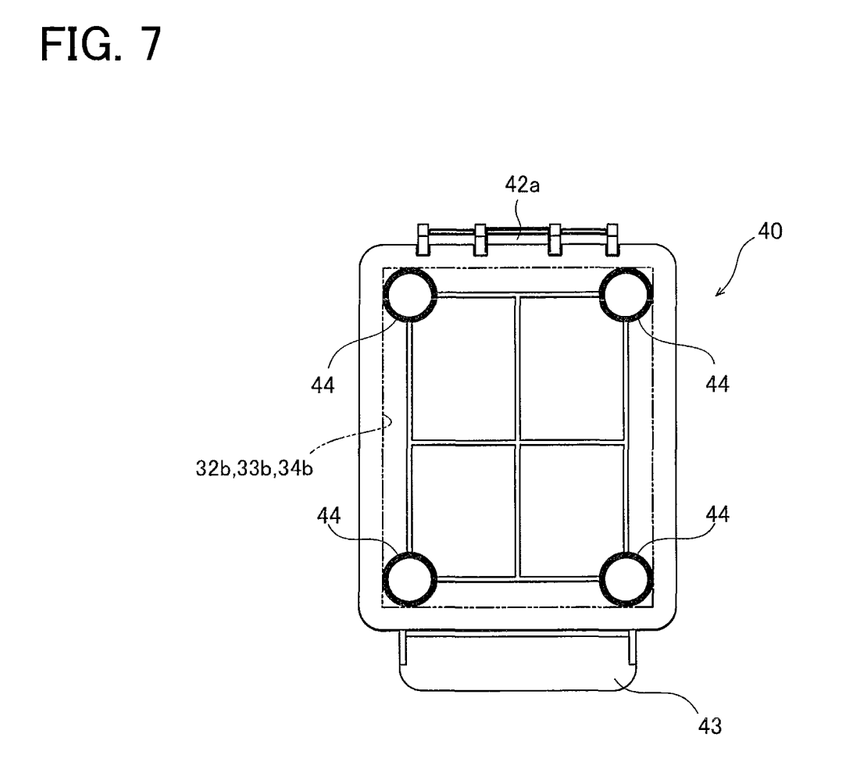
FIG. 7 is bottom view of the tray shown in FIG. 5.
Figure 8:
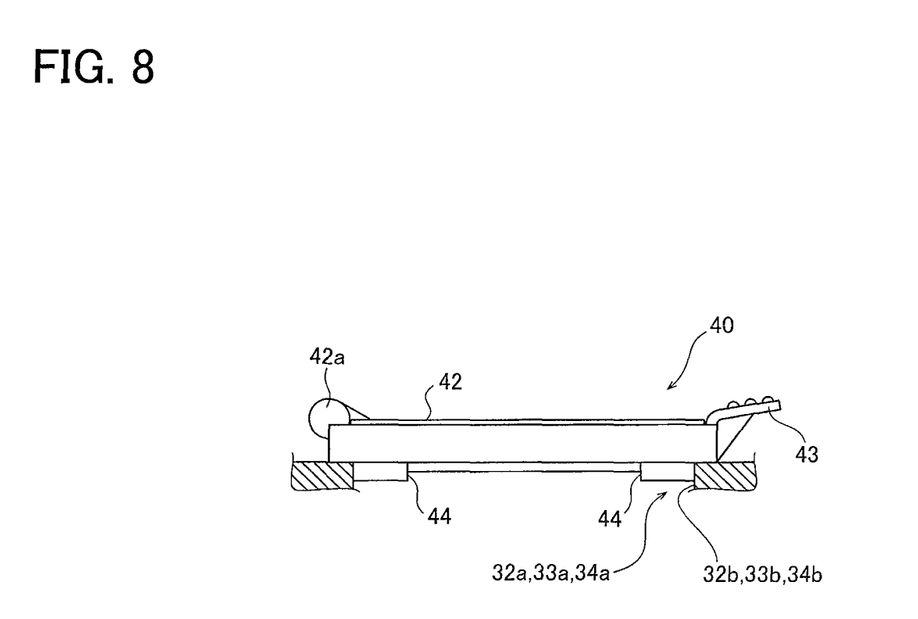
FIG. 8 is a schematic partial sectional view showing the tray from FIG. 5 installed in the tray placing section.

The convex feet 44 are provided at four locations to form a square on the under-side surface of the tray 40, as shown in FIGS. 7 and 8. Each foot 44 has a circular shape when viewed from the bottom surface side. As will be described later, the feet 44 are configured to engage the engaging parts 32b through 34b which are concave recess or hole of the tray placing units 32a through 34a when the tray 40 is installed on the tray placing units 32a through 34a provided on the three lid placing sections 32 through 34.

As shown in FIGS. 3, 4, and 9, the tray placing units 32a through 34a are provided to hold the tray 40 in the respective lid placing sections 32 through 34. As shown in FIG. 3, the tray placing section 34a provided in the lid placing section 34 and the tray placing section 32a provided in the lid placing section 32 have identical shapes and are respectively provided on the cover 35 and on the light source cover 36. As shown in FIG. 9, the tray placing section 33a provided in the lid placing section 33 is arranged at a predetermined position within the cover 35 (refer to FIG. 4). The tray placing sections 32a through 34a have engaging parts which are concave recesses or holes. Note that the cover 35 is configured to cover the lid placing section 33 including the tray 40 when the tray 40 is installed in the tray placing section 33a.

Specifically, the tray placing section 32a on the cover 35 and the tray placing section 34a on the light source cover 36 respectively have square concave engaging parts 32b (34b) on the top surface thereof, as shown in FIG. 3. As shown in FIG. 9, the tray placing section 33a on the inside of the cover 35 also has a square hole engaging part 33b. The feet 44 arranged in a square on the under-side surface of the tray 40 are inserted into the engaging parts 32b through 34b, such that the inner surface of the engaging parts 32b through 34b mutually engage the outer surface of the feet 44, as shown in FIG. 8. The engagement between the trays 40 and the tray placing sections 32a through 34a can be released to remove the tray 40 by gripping the handle 43 of the tray 40 and lifting the tray 40 upward (Z1 direction).

As shown in FIG. 9, a square, open-top box-like storage compartment 37 is provided below the tray placing section 33a which is arranged inside of the cover 35. The storage compartment 37 is continuous with the hole-like engaging part 33b, and the engaging part 33b becomes the inlet aperture of the storage compartment 37. The storage compartment 37 is configured so that the inner part is closed by the tray 40 being installed in the tray placing section 33a (refer to FIG. 4). The storage compartment 37 may be used to store, for example, attachments and tools used during maintenance of the sample analyzer 1.

The three lid placing sections 32 through 34 can accommodate a maximum of 27 large lids 8a when each of the trays 40 holds 9 lids 8a. Therefore, the lids 8a of all reagent containers 8 can be classified and placed in the lid placing sections 32 through 34 even when reagent containers 8 fill all 26 mounting apertures 15b of the container setting unit 15.

The effect of the sample analyzer 1 of the present embodiment is described below.

When operating the sample analyzer 1, the user opens the door 4a of the housing 4 to set the respective liquid containers, that is, the washing solution container 5, diluting liquid container 6, washing solution container 7, and reagent containers 8 in the container setting units 13 through 15 (refer to FIG. 2), as shown in FIG. 1. The lids 5a through 8a of each container are then removed. As shown in FIG. 2, when the large washing solution container 5, diluting liquid container 6, and washing solution container 7 are set in the mounting apertures 13a, 14a, and 15a, the lids 5a, 6a, and 7a are respectively placed in the lid placing sections 16a, 16b, and 16c which are adjacent to the mounting apertures 13a, 14a, and 15a in the X direction. The relational correspondence between container and lid therefore can be comprehended in a glance by storing the lids 5a, 6a, and 7a in this way.

When the small and intermediate reagent containers 8 are set in the mounting apertures 15b, the lids 8a are placed in a predetermined divided area of the tray 40 in the lid placing sections 32 through 34. The lids 8a can be organized to prevent any mistakes in the relational correspondence between lid and container even when various types of reagent containers 8 are used because the user places the lid 8a according to the display in the display area 42b of the dividing member 42. When reagent adheres to the inside of the lid 8a, the reagent is prevented from adhering to another lid 8a of another reagent container 8 because an absorbing member 45 is arranged between the tray 40 and the dividing member 42.

Each day when the sample analyzer 1 is shut down and ceases operation, the refrigeration function of the container setting units 13 through 15 shuts off and the liquid containers, that is, the washing solution container 5, diluting liquid container 6, washing solution container 7, and reagent container 8 are stored in a refrigerator within the facility to prevent deterioration and evaporation of the liquids. The user therefore removes the liquid containers 5 through 8 from the container setting units 13 through 15, recaps the liquid containers with the corresponding lids 5a through 8a, and stores the capped liquid containers in the refrigerator. Since the liquid containers 5 through 8 and the lids 5a through 8a are in an associated condition when the lids are placed at predetermined positions in the lid placing sections 16a through 16c and 32 through 34, the user installs the lid on the container and stores the container without losing the lid or returning the lid to the wrong liquid container.

In the present embodiment, the user can place the lids 5a through 8a of the liquid containers 5 through 8 set in the container setting units 13 through 15 in the lid placing sections 16a through 16c by providing the lid placing sections 16a through 16c and 32 through 34 in which to place the lids 5a through 8a of the liquid containers, that is, the washing solution containers 5, diluting liquid containers 6, washing liquid containers 7, and reagent containers 8 as described above. As a result, the lids 5a through 8a of the liquid containers 5 through 8 can be stored without loss. By arranging the lid placing sections 16a through 16c and 32 through 34 near the container setting units 13 through 15 or on the front side of the container setting units 13 through 15, the user can observe the vicinity or front side of the container setting units 13 through 15 when installing the liquid containers 5 through 8 in the container setting units 13 through 15 and when removing the lids 5a through 8a, and the removed lids 5a through 8a can be placed in the lid placing sections 16a through 16c and 32 through 34 which are installed at easily accessible positions. As a result, forgetting where the lid was placed is avoided, and the work of the user is reduced thus improving the usability of the apparatus.

In the present embodiment described above, the lid placing sections 32 through 34 are provided in the transporting apparatus 3 on the front side of the container setting units 15. In this way the user can place the lids 8a of the reagent containers 8 in the transporting apparatus 3 at the same location as the rack R holding the sample containers T is set, thus allowing easy placing and organization of the lids 8a and avoiding forgetting where the lids 8a are placed. Since the lid placing sections 32 through 34 are provided in the transporting apparatus 3 on the front side (Y2 direction side), they are more readily accessible to the user compared to placement within the housing 4 inside the measuring device 2, thus improving the ease of the lid placing operation and lid removing operation performed by the user.

In the present embodiment described above, the lid placing sections 32 through 34 are aligned with the transport path 31 in a different region from the region in which the transport path 31 is provided. In this way placing the lids 5a through 8a can be easily organized when the rack R holding the sample containers T is installed in the transport path 31 or when the rack R holding the sample containers T is being transported.

In the present embodiment described above, the lid placing sections 32 and 33, and the lid placing section 34 are provided on both sides of the transport path 31 in the X direction so that the transport path 31 is interposed therebetween. Therefore, a larger lid placing area for the lids 8a is ensured even when a large number of liquid containers (and thus a large number of lids) is used in the sample analyzer 1. Placement of the lids 8a is selective inasmuch as the most convenient lid placing area can be selected from among the lid placing sections 32 through 34 on bilateral sides.

In the present embodiment described above, the tray 40 capable of accommodating a plurality of lids 8a, and tray placing section 32a through 34a are provided in the lid placing sections 32 through 34. The engaging parts 32b through 34b are provided on the top surface of the tray placing sections 32a through 34a, and feet 44 are provided to be fittedly engage the engaging parts 32b through 34b. Accordingly, the lid 8a on the tray 40 can be carried to a workbench when installing the lid 8a on the reagent container 8 since the lid 8 of the reagent container 8 can be moved for each tray. The situation of the user dropping the tray 40 is prevented by the engagement between the engaging parts 32b through 34b and the feet 44. In the present embodiment described above, the lids 8a are easily carried on the tray 40 because the tray 40 is provided with a handle 43.

In the present embodiment described above, the storage compartment 37 is provided below the tray placing section 33a of the lid placing section 33. The storage compartment 37 is configured so that the inside area of the storage compartment 37 is closed by the tray 40 installed on the tray placing section 33a. The convenience of the sample analyzer 1 is improved for the user who is no longer concerned about losing components because attachments in addition to the lids 8a of the reagent containers 8 can also be stored in the storage compartment 37.

The present embodiment described above prevents contamination by foreign matter being introduced into the reagent container 8 when the lid 8a is reseated on the reagent container 8 by providing the cover 35 to cover the lid placing section 33. The present embodiment described above ensures abundant locations to place the lids 8a by also providing the lid placing sections 32 on the top surface of the cover 35.

In the present embodiment described above, the lid placing sections 32 through 34 are provided with a tray 40 and dividing member 42 which has sufficient area to accommodate a plurality of lids 8a. Since the lids 8a can be classified and organized when placed in the divided placement area, organization and management of the reagent containers 8 including the lids 8a can be easily accomplished.

In the present embodiment described above, the lid placing sections 32 through 34 are provided outside the housing 4, and the lid placing sections 16a through 16c are provided inside the housing 4. Therefore, a larger lid placing area for the lids 5a through 8a is ensured even when a large number of liquid containers 5 through 8 is used in the sample analyzer 1.

In the present embodiment described above, the lid placing sections 32 and 33 are arranged on the front side of the container setting unit 15 viewed from the front side (Y2 direction side) of the sample analyzer 1, that is, the same side as the door 4a and container setting unit 15 are on (X2 direction side). Therefore, the user can install and remove the reagent containers 8, store the lids 8a, and install the lid 8s on the removed reagent container 8 at the same position on the X2 direction side of the sample analyzer 1. As a result, the operation of setting the reagent container 8 and the operation of storing a reagent container 8 in a refrigerator within the facility are improved.

Note that the embodiment of the present disclosure is an example in all aspects and not to be considered limiting in any way. The scope of the present invention is expressed by the scope of the claims and not by the description of the embodiment, and includes all meanings and equivalences and modifications pertaining thereunto.

For example, although the above embodiment is described by way of example in which the lid placing sections 16a through 16c are positioned near the container setting units 13 through 15 inside the housing 4, and the lid placing sections 32 through 34 are positioned on the front side of the container setting units 13 through 15 outside the housing 4, the present invention is not limited to this configuration. In the present invention, the lid placing sections also may be positioned only near the container setting units inside the housing, or the lid placing sections may be positioned only in front of the container setting units. Moreover, the lid placing sections also may be arranged on the front side of the container setting units inside the housing.

Although the above embodiment is described by way of example in which the lid placing sections are provided in a sample analyzer 1 which has a measuring device 2 and a transporting apparatus 3, the present invention is not limited to this configuration. In the present invention, the lid placing sections also may be provided in an independent transporting apparatus which can be connected to the sample analyzer that only has a measuring device.

Although the above embodiment is described by way of example in which the lid placing sections are provided on the outer X direction side of the transport path alongside the transport path of the transporting apparatus, the present invention is not limited to this configuration. For example, the lid placing sections also may be provided at positions on the front side (Y2 direction side) of the transport path. The lid placing sections also may be configured so as to be pulled from the bottom of the transport path, the lids placed when the lid placing section is pulled from the front side (Y2 direction side), then returned to the bottom of the transport path.

Although the above embodiment is described by way of example in which the lid placing sections are arranged on both side of the transport path in the X direction so as to sandwich the transport path therebetween, the present invention is not limited to this configuration. For example, the lid placing sections also may be arranged on only the X1 direction side or the X2 direction side.

Although the above embodiment is described as having three lid placing sections 32 through 34 in the transporting apparatus, the present invention is not limited to this configuration. In the present invention, one, two or four or more lid placing sections also may be provided in the transporting apparatus.

Although the above embodiment is described as having a tray 40 in the lid placing sections 32 through 34, the present invention is not limited to this configuration. In the present invention, the tray may be omitted, and the lid placing section may be configured to accommodate the lid directly on the lid placing section.

Although the above embodiment is described by way of example in which engaging parts 32b through 34b are provided on the tray placing sections 32a through 34a and feet 44 are provided on the tray 40 such that the engaging parts 32b through 34b and feet 44 mutually engage, the present invention is not limited to this configuration. In the present invention, the tray may be simply placed on the tray placing section without engagement between the tray and the tray placing section. When there is no engagement between the tray and the tray placing section, the tray itself may be configured to be fitted to the tray placing section without providing feet on the tray.

Although the above embodiment is described by way of example in which a storage compartment 37 is provided below the tray placing section 33a and the storage compartment 37 is configured so as to be closed by the tray 40, the present invention is not limited to this configuration. In the present invention, the storage compartment may be omitted. When the storage compartment is provided, an operating member (lid part) may be provided to open and close the entrance rather than closing the storage compartment via the tray.

Although the above embodiment is described by way of example in which a handle is provided on the tray, the present invention is not limited to this configuration and the handle may be omitted from the tray.

Although the above embodiment is described in terms of providing a cover 35 to cover the lid placing section 33 and providing a lid placing section 32 on the top surface of the cover 35, the present invention is not limited to this configuration inasmuch as the cover 35 may be omitted. When the cover 35 is provided, the lid placing section may be omitted on the top surface of the cover 35.

Although the above embodiment is described in terms of providing the dividing member 42 to divide the placing area of the tray 40 into nine areas in a 3×3 pattern, the present invention is not limited to this configuration. In the present invention, the dividing member may be omitted from the tray. When the dividing member is provided, the placing region may be divided into more or fewer areas than the nine areas of the example. For example, large lids 5a, 6a, and 7a may be placed on a tray divided into four areas in a 2×2 pattern. In this case, trays capable of accommodating large lids and tray capable of accommodating small lids may have different numbers of divided areas.

Although the above embodiment is described in terms of configuring the lid placing sections 16a through 16c within the housing 4 to accommodate large lids 5a through 7a, and the lid placing sections 32 through 34 outside the housing 4 are configured to accommodate small lids 8a, the present invention is not limited to this example. In the present invention, the lid placing sections inside the housing also may be configured to accommodate small lids, and the lid placing sections outside the housing may be configured to accommodate large lids.

Although the above embodiment is described by way of example in which the lid placing sections 16*a* through 16*c* inside the housing 4 are arranged adjacently and respectively associated with the washing solution container 5, diluting liquid container 6, and washing solution container 7, the present invention is not limited to this example. In the present invention, the lid placing sections also may be arranged a distance from the liquid containers. In this case, the lid placing sections may be provided together in a predetermined area separately from the position of the respective liquid container.

Although the above embodiment is described in terms of washing solution container 5 and 7, diluting liquid container 6, and reagent container 8 as examples of liquid containers, the present invention is not limited to this example. In the present invention, the liquid container also may be containers containing liquids such as calibrator (calibration material) and control (standard sample) in addition to washing solution containers, diluting liquid container, and reagent containers insofar as the container holds a liquid used in the measuring device.

What is claimed is:

1. A sample analyzer, comprising:
   a container setting unit for setting a plurality of liquid containers accommodating liquids, the liquid containers associated with lids for removably covering an internal empty space of the liquid containers;
   a detecting unit configured to perform a measurement operation for a sample using the liquid;
   a liquid suctioning unit including a suction tube for suctioning the liquid from at least one of the plurality of liquid containers; and
   a lid placing section for placing one or more lids of the plurality of the liquid containers while the lids are removed from the liquid containers, the lid placing section comprising a tray with an area for placing a plurality of lids, and a dividing member provided on the tray to divide the area, wherein the lid placing section is separated from the container setting unit and, the container setting unit is arranged in a housing with the detecting unit and the liquid suctioning unit and the lid placing section is arranged outside of the housing and positioned adjacent or on the front side from a location of the housing where the container setting unit is positioned;
   wherein the dividing member is connected to the top of the tray so as to be openable and closable relative to the tray; and
   the lid placing section retains an absorbing member between the tray and the dividing member.

2. The sample analyzer of claim 1, further comprising:
   a transporting apparatus configured to transport sample containers containing samples; and
   a sample suctioning unit configured to suction a sample accommodated in a sample container transported by the transporting apparatus.

3. The sample analyzer of claim 2, wherein
   the transporting apparatus comprises a transport path extending in a longitudinal direction and configured to transport the sample containers; and
   the lid placing section is arranged in an outside of a region in which the transport path is provided.

4. The sample analyzer of claim 3, wherein
   the lid placing section comprises a first lid placing section at one end of the transport path and a second lid placing section at the other end of the transport path, wherein the first lid placing section, the second lid placing section and the transport path are aligned in the longitudinal direction of the transport path where the transport path extends, and the first lid placing section and the second lid placing section sandwich the transport path in the longitudinal direction of the transport path.

5. The sample analyzer of claim 1, wherein the lid placing section comprises a concave shaped space to accommodate the lid.

6. The sample analyzer of claim 1, wherein
   the lid placing section is divided into a plurality of areas, each area accommodating the lids one by one.

7. The sample analyzer of claim 6, wherein
   each area is sized to match size of a lid for a reagent container.

8. The sample analyzer of claim 1, wherein
   the lid placing section further comprises a tray placing section for removably installing the tray;
   wherein the tray placing section has a first engaging part on the top surface thereof, and
   the tray has a second engaging part which fittedly engages the first engaging part when the tray is installed in the tray placing section.

9. The sample analyzer of claim 1, wherein
   the lid placing section further comprises a tray placing section for removably installing the tray;
   the sample analyzer further comprises a storage compartment which is provided below the tray placing section;
   the storage compartment is configured so that the inner area is closed when the tray is installed in the tray placing section.

10. The sample analyzer of claim 8, wherein
    the tray has a handle for carrying the tray.

11. The sample analyzer of claim 1, further comprising:
    a cover configured to cover the lid placing section.

12. The sample analyzer of claim 11, further comprising:
    another lid placing section for placing a lid of at least one of the plurality of the liquid containers, wherein
    another lid placing section is provided on the top surface of the cover.

13. The sample analyzer of claim 1,
    wherein the lid placing section further comprises a display area provided on the dividing member to show a plurality of types of reagents accommodated in a reagent container associated with a lid.

14. The sample analyzer of claim 1, further comprising:
    a housing configured to accommodate the liquid suctioning unit and the container setting unit inside, wherein
    the housing further accommodates another lid placing section inside of the housing.

15. The sample analyzer of claim 14, wherein
    said another lid placing section is arranged adjacent to the plurality of liquid containers set on the container setting unit.

* * * * *

UNITED STATES PATENT AND TRADEMARK OFFICE
CERTIFICATE OF CORRECTION

PATENT NO. : 9,702,888 B2
APPLICATION NO. : 14/226504
DATED : July 11, 2017
INVENTOR(S) : Hiroyuki Matsuura et al.

It is certified that error appears in the above-identified patent and that said Letters Patent is hereby corrected as shown below:

In the Claims

Column 14, Claim 3, Line 1, after "the lid placing section is arranged" delete "in an".

Signed and Sealed this
Twenty-fourth Day of April, 2018

Andrei Iancu
*Director of the United States Patent and Trademark Office*